United States Patent

Bernáth et al.

[11] Patent Number: 4,622,327
[45] Date of Patent: Nov. 11, 1986

[54] 2H-AZETO[2,1-a]-ISOQUINOLINE DERIVATIVES AND PHARMACEUTICAL COMPOSITIONS CONTAINING THEM

[75] Inventors: Gábor Bernáth; Jenö Kóbor, both of Szeged; Alajos Kálmán; Pál Sohár, both of Budapest; Ferenc Fülöp, Szeged; Elemér Ezer, Budapest; György Hajós, Budapest; Éva Pálosi, Budapest; László Dénes, Budapest; László Szporny, Budapest, all of Hungary

[73] Assignee: Richter Gedeon Vegyeszeti Gyar R.T., Budapest, Hungary

[21] Appl. No.: 664,786

[22] Filed: Oct. 25, 1984

[30] Foreign Application Priority Data

Oct. 25, 1983 [HU] Hungary ............... 3655-83

[51] Int. Cl.⁴ ............ A61K 31/40; C07D 455/08
[52] U.S. Cl. ....................... 514/294; 546/94
[58] Field of Search ............. 546/94; 514/294

[56] References Cited
FOREIGN PATENT DOCUMENTS
1242175 3/1969 United Kingdom ............ 546/94

Primary Examiner—Henry R. Jiles
Assistant Examiner—J. Richter
Attorney, Agent, or Firm—Keil & Weinkauf

[57] ABSTRACT

The invention relates to new 2H-azeto[2,1-a]isoquinoline derivatives of formula (I)

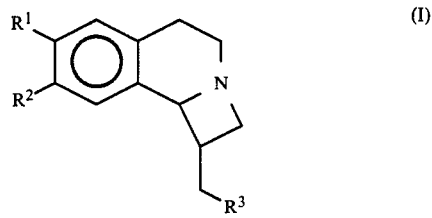

wherein
R¹ and R² represent hydroxyl or alkoxy having from 1 to 6 carbon atoms,
R³ is hydroxyl, halogen or an

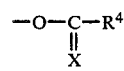

group,
wherein
X is oxygen or sulfur,
R⁴ is optionally substituted phenyl,
and acid addition, metal and quaternary salts thereof.

According to the invention the new compounds are prepared by cyclization of the corresponding compounds of formula (II),

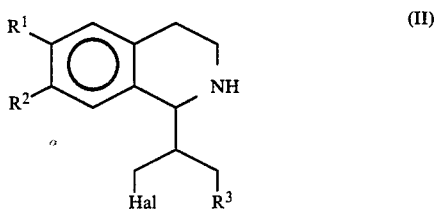

wherein R¹, R² and R³ are as defined above, and Hal is halogen.

Compounds of formula (I) are pharmaceutically active, in particular are potent analgesic and antipyretic agents.

8 Claims, No Drawings

2H-AZETO[2,1-A]-ISOQUINOLINE DERIVATIVES AND PHARMACEUTICAL COMPOSITIONS CONTAINING THEM

The invention relates to new 2H-azeto[2,1-a]isoquinoline derivatives of formula (I),

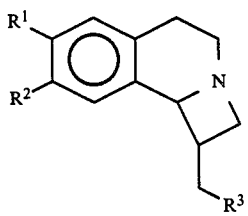

wherein
$R^1$ and $R^2$ represent hydroxyl or alkoxy having from one to 6 carbon atoms,
$R^3$ is hydroxyl, halogen or an

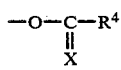

group,
in which
$R^4$ is optionally substituted phenyl,
X is oxygen or sulfur,
and acid addition, metal and quaternary salts thereof.

According to another aspect of the invention, there is provided a process for the preparation of the compounds of formula (I) ($R^1$, $R^2$ and $R^3$ are as defined above) and salts thereof, which process comprises cyclizing a compound of formula (II),

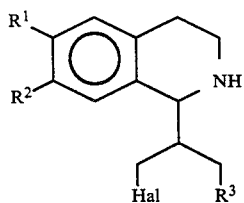

in which
$R^1$, $R^2$ and $R^3$ are as defined above, and
Hal is halogen,
or an acid addition salt thereof in an alkaline or neutral medium, and, if desired,
in a compound of the formula (I) obtained converting the group $R^1$ and/or $R^2$ and/or $R^3$ into another group within the definition of $R^1$, $R^2$ and $R^3$ and/or, if desired,
converting a compound of the formula (I) obtained into a salt thereof, or
from a salt obtained liberating the corresponding free base of the formula (I).

Compounds of the formula (I) are biologically active, in particular show antipyretic, analgesic, gastric acid secretion inhibiting and antiallergic activity.

The term "alkoxy having from one to 6 carbon atoms" in the definition of $R^1$ and $R^2$ is used to refer to straight-chained or branched alkoxy groups, e.g. methoxy, ethoxy, n-propoxy, isopropoxy, n-butoxy, isobutoxy, sec.-butoxy, tert.-butoxy, n-pentoxy, isopentoxy, n-hexyloxy, isohexyloxy, etc. groups.

The starting compounds of the formula (II) are new. Their preparation is disclosed in our co-pending Hungarian patent application No. 3653/83, which application was filed in the United States on Oct. 25, 1984 and was given Ser. No. 664,849. Most preferably, in a first step analogous compounds, in which $R^3$ is hydroxyl and which contain hydroxyl instead of "Hal", are prepared by reacting the corresponding 1-methyl-3,4-dihydroisoquinoline or 1-($\beta$-hydroxyethyl)-3,4-dihydroisoquinoline derivatives with formaldehyde, or the hydrate or trimeric derivative thereof, in an alkaline medium and by subsequent hydrogenation. In the compounds obtained one of the hydroxyl groups can then be replaced by a halogen atom and the other one by any group given in the definition of $R^3$, by methods known in the art.

The ring closure of the compounds of formula (II) is preferably carried out in an inert organic solvent, preferably in an aliphatic alcohol having from 1 to 6 carbon atoms, e.g. methanol or ethanol, in a ketone, e.g. acetone, or in an aromatic hydrocarbon, e.g. benzene. If compounds of formula (II) are used in the form of their acid addition salts, the medium should be rendered alkaline by addition of a suitable base. For this purpose for example an alkali metal hydroxide, e.g. sodium hydroxide can be employed. The base added to the reaction mixture liberates the free base of formula (II) from its acid addition salt and serves as a catalyst in the ring closure reaction. Under these conditions ring closure takes place at about room temperature, but slightly elevated temperatures accelerate the reaction. If a free base of the formula (II) is used as a starting material in the reaction, ring closure takes place at an elevated temperature, preferably at about the boiling point of the reaction mixture. The reaction time and temperature are functions of other reaction conditions, e.g. reactants and the medium employed.

2H-azeto(2,1-a)isoquinoline derivatives substituted in position 1 by phenyl-methyl group are described under C.A.S registry Nos. 51452-45-0 and 51517-68-1.

The compounds of formula (I) prepared according to the invention may, if desired, be converted into their acid addition salts by reaction with an acid according to methods known per se. The preferred acids include pharmaceutically acceptable acids. Similarly, compounds of formula (I) may be converted into the corresponding quaternary salts by quaternization methods well known in the art.

Salt formation can be carried out, for example, in an inert organic solvent such as a $C_{1-6}$ aliphatic alcohol, in such a way that the racemic or optically active compound of formula (I) is dissolved in the solvent and the selected acid or a solution thereof formed with the same solvent is added to the first solution until it becomes slightly acidic. Thereafter the acid addition salt separates out and may be removed from the reaction mixture e.g. by filtration.

If desired, compounds of the formula (I) or salts thereof may be further purified, for example by recrystallization. Solvents suitable for this purpose are selected depending on the solubility and crystallization properties of the substances to be crystallized.

If desired, compounds of formula (I) obtained in salt form may be liberated from their salts in a manner known per se.

In the compounds of formula (I) the groups $R^1$ and/or $R^2$ and/or $R^3$ may be converted into other groups within the definition of $R^1$, $R^2$ and $R^3$, respectively. For example compounds of the formula (I), in which $R^1$ and/or $R^2$ is hydroxyl, may be converted into the corresponding alkoxy compounds by conventional etherization methods. Methylation is preferably carried out with diazomethane or dimethyl sulfate, while the ethers containing higher alkyl groups may, for example, be prepared with alkyl iodides. Similarly, the compounds containing alkoxy groups as the above-mentioned substituents may be converted into the corresponding hydroxy derivetives by conventional techniques, e.g. by heating with hydrogen iodide or in the presence of anhydrous aluminium chloride. Compounds of formula (I), in which $R^3$ is hydroxyl, can be prepared also through the corresponding halogen derivatives, while the group

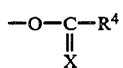

can be prepared also subsequently, using any acylating agent suitable for the introduction of this group. Suitable acylating agents include carboxylic acid halides and anhydrides, preferably carboxylic acid chlorides.

As mentioned before, compounds of formula (I) are pharmaceutically active, in particular show valuable analgesic and antipyretic activity.

For the pharmacological tests CFLP (LATI) mice of both sexes, weighing 18 to 22 g each and male Han. Wistar (LATI) rats weighing 160 to 180 g each were used. The test materials were administered orally, in 30 mg/kg doses, in the form of a suspension containing 5% of Tween 80, one hour before the tests.

TEST METHODS

1. Maximum electroshock (mice)

The shock was applied through a corneal electrode (20 mA, 0.2 msec, HSE Schockgerät typ. 207). The animals which do not show a tonic, extensoric spasm as a result of electroshock treatment are considered protected (see Swinyard et al.: J. Pharmacol. Exp. Ther. 106, 319/1952/).

2. Metrazole spasm (mice)

After pretreatment the animals were administered 125 mg/kg of pentylenetetrazole subcutaneously. The animals, which did not show (a) a clonic, (b) a tonic extensoric spasm and which survived the experiment, were regarded as protected.

Observation time: one hour (Everett L. M. and Richards R. K.: J. Pharmacol. Exp. Ther. 81, 402/1944/).

3. Inhibition of tetrabenazine catalepsy

The test was carried out on male rats each weighing 160 to 180 g. The test materials were administered intraperitoneally, in a dose of 30 mg/kg, one hour before tetrabenazine administration. The animals, which if their forelegs were placed on a 7 cm high pillar, did not correct their bizarre position within 30 seconds were regarded as cataleptic (Delay J. and Denicker P.: Compt. Rend. Congr. Med. Alenistens Neurologists, 19, 497/Luxemb./).

4. Analgesic activity (mice)

One hour after pretreatment, mice were administered 0.4 ml of a 0.6% acetic acid solution intraperitoneally, as a pain stimulus. The frequency of writhing syndrome is registered for 30 minutes. The changes observed as a result of treatment with the test compounds is related to the mean value of the frequency of writhing syndrome in the control group, and the difference is expressed in percentage (Koster R. et al.: Exp. Ther. 72:74/1941/).

5. Antipyretic activity (rats)

Hyperthermia is induced in rats with Brewer's yeast suspension (0.5% of Brewer's yeast, 1% of arabic gum in a volume of 0.3 ml, s.c.). The animals are treated with the test materials 4 hours later, and the tracheal temperature of the animals is registered with an ELAB thermometer (typ. TE-3) for 4 hours. The antipyretic activity is expressed in percentage of the animals which have an at least one centrigrade lower temperature than the average of the temperature of the control group treated with the solvent (Nimegeers C. J. E. et al.: Arzneimittel Forsch. 25:15/9/1975/).

The pharmacological results are set forth in Table 1.

Compound A = 1-(chloromethyl)-7,8-dimethoxy-1,4,5,9b-tetrahydro-2H-azeto[2,1-a]isoquinoline hydroiodide Compound B = 1-(chloromethyl)-7,8-diethoxy-1,4,5,9b-tetrahydro-2H-azeto[2,1-a]isoquinoline hydrochloride

TABLE 1

| Substance | Antispasm activity | | | Antitetrabenazine activity (%) | Analgesic activity (%) | Antipyretic activity (%) |
| --- | --- | --- | --- | --- | --- | --- |
| | max. electroshock | metrazole a | b | | | |
| Compound A | — | — | 20.0 | — | 30.0 | 75.0[x] |
| Compound B | 20.0 | — | 24.0 | — | 20.0 | 30.0 |
| Na—salycilate | — | — | 20.0 | — | 113.0[x] | 110.0[x] |

— = ineffective
[x] = ED$_{50}$ (mg/kg, p.o.)

The results show that the analgesic activity of the test compounds is better than that of Na-salicylate. While the latter compound is ineffective when administered in a dose of 30 mg/kg, in the above test compound A decreases the frequency of acetic acid-induced writhing syndrome by about 30% in a dose of 30 mg/kg. Moreover, compound A is one and a half-times more potent antipyretic agent than Na-salicylate.

The new compounds of the general formula (I) or pharmaceutically acceptable acid addition salts thereof may be formulated for therapeutic purposes. The invention therefore also relates to pharmaceutical formulations containing at least one compound of the general formula (I)—wherein R, A and B are as described above—or pharmaceutically acceptable salts thereof, in admixture with inert, non-toxic carriers conventional for this purpose and suitable for parenteral or enteral administration and/or other additives. As carriers solid or liquid compounds, for example water, gelatine, lactose, milk sugar, starch, pectine, magnesium stearate, stearic acid, talc, vegetable oils, such as peanut oil, olive oil, arabic gum, polyalkylene glycols, and vaseline can be used. The compounds can be formulated as conventional pharmaceutical formulations, for example in a solid (globular and angular pills, suppositories) or liquid (oily or aqueous solutions, suspensions, emulsions, syrups, soft gelatine capsules, injectable oily or aqueous solutions or suspensions) form. The quantity of the solid carrier can be varied within wide ranges, but preferably is between 25 mg. and 1 g. The compositions optionally contain also conventional pharmaceutical additives, such as preserving agents, stabilizing agents, emulsifying agents, wetting agents, salts for adjusting the osmotic pressure, buffers, flavouring and aroma materials. The compositions according to the invention optionally contain the compounds of the general formula (I) in association with other, known active ingredients. The unit doses are selected depending on the way of administration. The pharmaceutical compositions are prepared by conventional techniques including sieving, mixing, granulation, pressing or dissolution of the ingredients. The formulations obtained are then subjected to additional conventional treatments, such as sterilization.

The invention is elucidated in detail by the aid of the following non-limiting Examples.

EXAMPLE 1

Preparation of
1-(chloromethyl)-7,8-dimethoxy-1,4,5,9b-tetrahydro-2H-azeto[2,1-a]isoquinoline hydroiodide 5.1 g (0.015 mole) of 1-[bis(chloromethyl)-methyl]-6,7-dimethoxy-1,2,3,4-tetrahydroisoquinoline hydrochloride are suspended in 24 ml of acetone. 6.0 ml of methanol containing 10% (0.015 mole) of sodium hydroxide are added to the suspension, whereupon the solution is filtered after 5 minutes. 2.3 g (0.0153 mole) of sodium iodide are added to the filtrate, which is allowed to stand for two days and the crystals separated out are filtered out by glass filter. Crystallization from a mixture of acetone and ether yields the aimed compound in the form of pale-beige crystals with a melting point of 202° to 205° C.

Yield: 4.6 g (78%).

Analysis for $C_{14}H_{19}ClINO_2$ (395.67): calculated: C 42.50%, H 4.84%, N 3.54%; found: C 43.07%, H 4.93%, N 3.41%.

EXAMPLE 2

Preparation of
1-(benzoyloxymethyl)-7,8-dimethoxy-1,4,5,9b-tetrahydro-2H-azeto[2,1-a]isoquinoline hydrochloride 0.01 mole (4.26 g) of 1-[1'-chloromethyl-1"-(benzoyloxymethyl)-methyl]-6,7-dimethoxy-1,2,3,4-tetrahydroisoquinoline hydrochloride is suspended in 20 ml of absolute acetone, and 5 ml of methanol containing 0.01 mole of sodium hydroxide are added to the suspension under slight heating. The precipitated sodium chloride is filtered off through a folding filter, whereupon the solution is boiled for 10 hours. After standing for 2 days at +4° C. the product is filtered off and is recrystallized from a mixture of ethanol and ether.

Melting point: 2.4° C. (61.5%).

Analysis for $C_{21}H_{24}ClNO_4$ (389.87): calculated: C 64.69%, H 6.20%, N 3.59%, Cl 9.09%; found: C 63.96%, H 6.49%, N 4.19%, Cl 9.50%.

EXAMPLE 3

Preparation of
1-(hydroxymethyl)-7,8-dimethoxy-1,4,5,9b-tetrahydro-2H-azeto[2,1-a]isoquinoline hydrochloride 0.01 mole (3.22 g) of 1-(benzoyloxymethyl)-7,8-dimethoxy-1,4,5,9b-tetrahydro-2H-azeto[2,1-a]isoquinoline hydrochloride is boiled in a mixture of 50 ml of a 5% hydrochloric acid solution and 20 ml of ethanol for 2 hours. The mixture is evaporated and the evaporation residue is triturated with ether to yield the aimed compound with a melting point (after recrystallization from ethanol) of 219° to 221° C. (decomp.).

Yield: 61%.

Analysis for $C_{14}H_{20}ClNO_3$ (285.76): calculated: C 58.85%, H 7.05%, N 4.90%, Cl 12.41%; found: C 58.59%, H 7.44%, N 4.67%; Cl 12.67%.

EXAMPLE 4

Preparation of
1-(hydroxymethyl)-7,8-dimethoxy-1,4,5,9b-tetrahydro-2H-azeto[2,1-a]isoquinoline hydrochloride By reacting 0.01 mole (3.22 g) of 1-[1'-(chloromethyl)-1"-(hydroxymethyl)-methyl]-6,7-dimethoxy-1,2,3,4-tetrahydroisoquinoline hydrochloride with sodium hydroxide according to Example 2, the aimed compound is obtained in a yield of 73%.

Melting point: 220° to 222° C.

The spectral data of the product are identical with those of the compound prepared in Example 3.

EXAMPLE 5

Preparation of
1-(benzoyloxymethyl)-7,8-dimethoxy-1,4,5,9b-tetrahydro-2H-azeto[2,1-a]isoquinoline hydrochloride 0.01 mole (1,85 g) of 1-(hydroxymethyl)-7,8-dimethoxy-1,4,5,9b-tetrahydro-2H-azeto[2,1-a]isoquinoline hydrochloride is acylated with benzoyl chloride following the conventional Schotten-Baumann acylation method.

Yield: 69%.

Melting point: 170° to 172° C.

The spectral data of the product are identical with those of the product of Example 2.

EXAMPLE 6

Preparation of
1-(chloromethyl-7,8-diethoxy-1,4,5,9b-tetrahydro-2H-azeto[2,1-a]isoquinoline hydrochloride Following the procedure described in Example 2 but using 1-[bis(chloromethyl)-methyl]-6,7-diethoxy-1,2,3,4-tetrahydroisoquinoline hydrochloride as a starting material, the aimed compound is obtained with a melting point of 130° to 131° C. (ethanol/ether).

Yield: 75%.

Analysis for $C_{16}H_{23}Cl_2NO_2$ (332.27): calculated: C 57.84%, H 6.98%, N 4.22%; found: C 57.52%, H 7.38%, N 4.35%.

EXAMPLE 7

Preparation of
1-(chloromethyl)-7,8-diethoxy-1,4,5,9b-tetrahydro-2H-azeto[2,1-a]isoquinoline 0.01 mole (3.69 g) of 1-[bis(chloromethyl)-methyl]-6,7-diethoxy-1,2,3,4-tetrahydroisoquinoline hydrochloride is suspended in 50 ml of absolute benzene, and 5 ml of triethyl amine are added to the suspension. After standing for 2 hours the reaction mixture is evaporated to dryness. The residue is dissolved in water and extracted with three 50-ml portions of ether. The ethereal extract is dried and evaporated to yield the aimed compound as a crystalline residue. After recrystallization from ether the product melts at 91° to 93° C.

Yield: 79%.

Analysis for $C_{16}H_{22}ClNO_2$: calculated: C 63.96%, H 7.49%, N 4.73%; found: C 64.98%, H 7.73%, N 4.61%.

Melting point of the corresponding hydrochloride: 129° to 130° C. The salt does not give any melting point depression when admixed with the product of Example 6.

We claim:

1. A compound of formula (I)

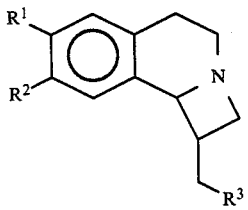
(I)

wherein
R¹ and R² represent hydroxyl or alkoxy having from 1 to 6 carbon atoms,
R³ is hydroxyl, halogen or an

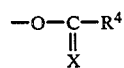

group,
in which
R⁴ is optionally substituted phenyl,
X is oxygen or sulfur,
and acid addition, metal and quaternary salts thereof.

2. A compound selected from the group of: 1-(chloromethyl)-7,8-dimethoxy-1,4,5,9b-tetrahydro-2H-azeto[2,1a]isoquinoline and hydroiodide thereof, 1-(benzoyloxymethyl)-7,8-dimethoxy-1,4,5,9b-tetrahydro-2H-azeto[2,1-a]isoquinoline and hydrochloride thereof, 1-(hydroxymethyl)-7,8-dimethoxy-1,4,5,9b-tetrahydro-2H-azeto[2,1-a]isoquinoline and hydrochloride thereof, 1-(chloromethyl)-7,8-diethoxy-1,4,5,9b-tetrahydro-2H-azeto[2,1-a]isoquinoline and hydrochloride thereof.

3. The compound of claim 1, which is 1-(chloromethyl)-7,8-dimethoxy-1,4,5,9b-tetrahydro-2H-azeto[2,1-a]isoquinoline hydroiodide.

4. The compound of claim 1, which is 1-(chloromethyl)-7,8-diethoxy-1,4,5,9b-tetrahydro-2H-azeto[2,1-a]isoquinoline hydrochloride.

5. A pharmaceutical composition having anti-pyretic, analgesic, gastric acid secretion inhibiting and anti-allergic properties comprising a pharmaceutically acceptable carrier or excipient and an effective amount for the desired property of a compound of the formula (I) as defined in claim 1.

6. A pharmaceutical composition having anti-pyretic, analgesic, gastric acid secretion inhibiting and anti-allergic properties comprising a pharmaceutically acceptable carrier or excipient and an effective amount for the desired property of a compound of the formula (I) as defined in claim 2.

7. A pharmaceutical composition having anti-pyretic, analgesic, gastric acid secretion inhibiting and anti-allergic properties comprising a pharmaceutically acceptable carrier or excipient and an effective amount for the desired property of a compound of the formula (I) as defined in claim 3.

8. A pharmaceutical composition having anti-pyretic, analgesic, gastric acid secretion inhibiting and anti-allergic properties comprising a pharmaceutically acceptable carrier or excipient and an effective amount for the desired property of a compound of the formula (I) as defined in claim 4.

* * * * *